US00PP10576P

United States Patent [19]

Bughrara et al.

[11] Patent Number: Plant 10,576

[45] Date of Patent: Aug. 25, 1998

[54] 'MOBUFF BUFFALOGRASS'

[75] Inventors: Suleiman Bughrara; John Dunn, both of Columbia, Mo.

[73] Assignee: The Curators of the University of Missouri, Columbia, Mo.

[21] Appl. No.: 846,267

[22] Filed: Apr. 30, 1997

[51] Int. Cl.[6] ..... A01H 5/00

[52] U.S. Cl. ..... Plt./90

[58] Field of Search ..... Plt./90

[56] References Cited

U.S. PATENT DOCUMENTS

| | | | |
|---|---|---|---|
| P.P. 7,539 | 5/1991 | Engelke et al. | Plt./88 |
| P.P. 8,475 | 11/1993 | Riordan et al. | Plt./90 |
| P.P. 8,896 | 9/1994 | Wu | Plt./90 |
| P.P. 8,897 | 9/1994 | Wu | Plt./90 |
| P.P. 9,208 | 7/1995 | Mancino | Plt./90 |

OTHER PUBLICATIONS

Reeder, J.R., "Notes on Mexican Grasses IX., Miscellaneous Chromosome Numbers—3", *Brittonia*, 23, 105–117 (Apr.–Jun. 1971).

Stebbins, G.L., "The Role of Polyploid Complexes in the Evolution of North American Grasslands", *Taxon*, 24, 91–106 (Feb. 1975).

Wu, L., et al., "Identifying Buffalograss [*Buchloe dactyloides* (Nutt.) Engelm.] Cultivar Breeding Lines Using Random Amplified Polymorphic DNA (RAPD) Markers", *J. Amer. Soc. Hort. Sci.*, 119, 126–130 (1994).

*Primary Examiner*—James R. Feyrer
*Assistant Examiner*—Kent L. Bell
*Attorney, Agent, or Firm*—Schwegman, Lundberg, Woessner & Kluth, P.A.

[57] ABSTRACT

A new and distinct variety of turf-type buffalograss called 'MoBuff' is characterized by its earlier spring greenup, better spring density, more numerous stolons, stolons having lower growth characteristics, and better green color characteristics when compared with commercially available turf-type buffalograsses. 'MoBuff' has been shown to perform well in a wide range of environmental conditions.

4 Drawing Sheets

FIELD OF THE INVENTION

The present invention relates to a new and distinct variety of diploid (2n=20) buffalograss characterized by its earlier spring greenup characteristics and its greener color when compared with commercially available turf-type buffalograsses. The claimed variety also has been shown to perform well in a wide range of environmental conditions.

BACKGROUND OF THE INVENTION

Buffalograss is a native North American short-prairie grass adapted to warm, semiarid and subhumid, unirrigated conditions. Buffalograss, *Buchloe dactyloides* (Nutt) Engelm., is a warm-season stoloniferous, sod-forming, perennial grass. It is a drought-tolerant and important range grass. It is well adapted to the prairies of Great Plains states and is an important grazing grass of the region. Buffalograss is found naturally from western Minnesota to central Montana, from Canada south to northwestern Iowa, Texas, western Louisiana, Arizona, and northern Mexico.

The buffalograss is the only species of its genus. It contains diploid, tetraploid, and hexaploid races (Stebbins, 1975), of which only the latter occur in the Great Plains area. The diploid race mainly occurs in Central Mexico and southern Texas (Reeder, 1971).

While buffalograss has long been used for range grazing and low-maintenance turf, its use in such applications waned as the use of irrigation increased. However, as new water-conservation measures have been sought, a resurgent need has arisen for lower quality, utility turfs for roadsides, airfields, lawns and other minimum maintenance areas. As such, significant effort has been expended in breeding and selection to improve the appearance of buffalograss. As a result, the physical characteristics of buffalograsses used for turf have improved. These characteristics include better green color, better sod-forming ability, higher density, shorter plant height, and finer leaf texture. As the appearance of buffalograsses has improved, they are increasingly being used in areas where ornamental and aesthetic turf is desired but where low maintenance and minimal irrigation is also desired. Such areas include golf course fairways and roughs, home lawns, highway right-of-ways, and commercial properties.

SUMMARY OF THE INVENTION

'MoBuff' is distinguished from existing varieties of buffalograss in that it is a vegetatively reproduced female plant having 2n chromosomes=20 (diploid). 'MoBuff' is distinguished in providing earlier spring greenup, better spring density, and better green color compared to other buffalograss genotypes, and hardiness in a wide range of environmental conditions and over a number of years. 'MoBuff' also has distinctive DNA-fingerprint profiles when compared to other market varieties.

DESCRIPTION OF THE CLAIMED VARIETY

Figure 2:
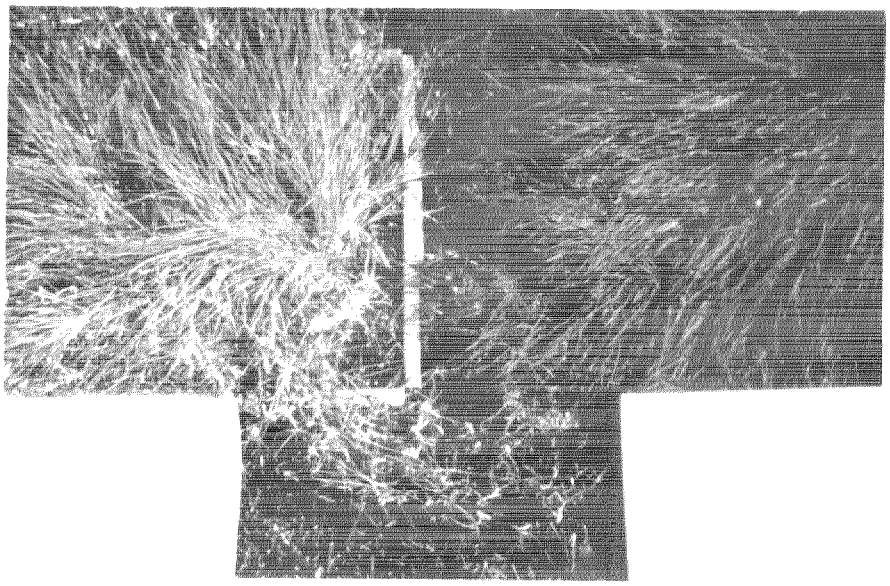
FIG. 2 is a photograph that depicts the buffalograss variety 'MoBuff' taken into a greenhouse in mid-winter along with 'Texoka' for comparison of greenup.
Figure 3:
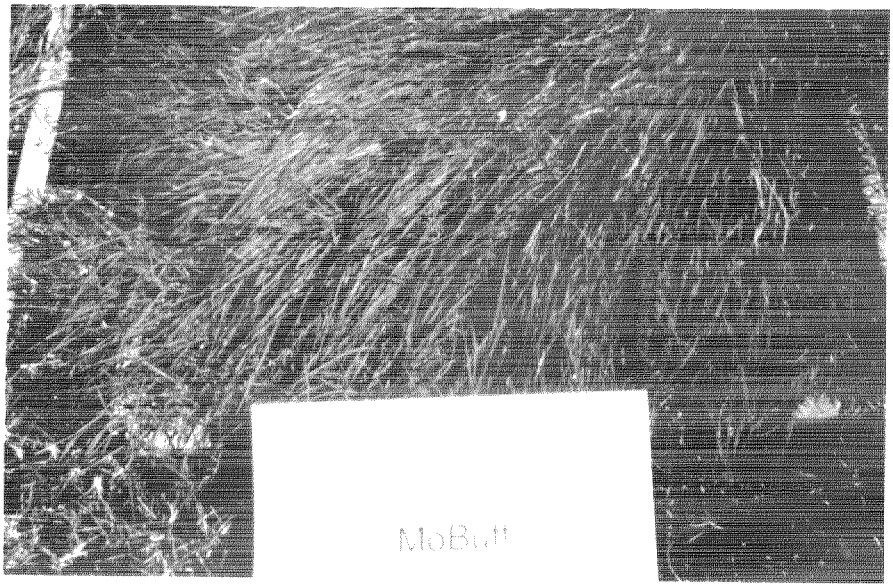
FIG. 3 is a photograph that depicts a rectangle of 'MoBuff' after greenup in a greenhouse.
Figure 5:
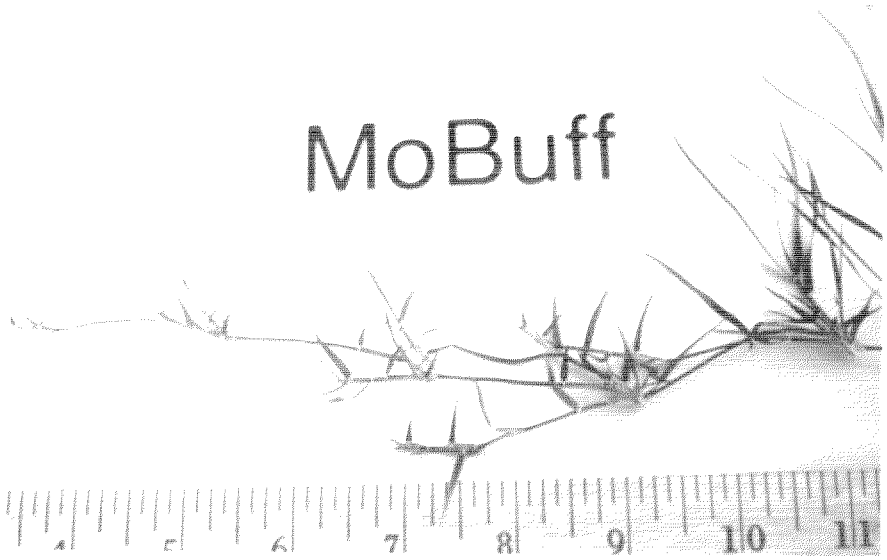
FIG. 5 is a photograph that depicts in detail the structure of portion of a single plant of 'MoBuff'.

The 'MoBuff' variety claimed herein, and shown in FIGS. 2, 3, and 5 meets each of the requirements of providing earlier spring greenup, better spring density, and better green color and offers aesthetics comparable to or better than other commercially available buffalograsses.

'MoBuff' is a vegetatively propagated female plant. A single plant plug, approximately 10 centimeters (cm) in diameter and 10 cm deep of the 'MoBuff' genotype was selected in 1974, and taken with a golf-green-cup cutter, from an area of buffalograss growing in a cultivated lawn of Kentucky bluegrass in the town of Columbia in central Missouri. The genotype was maintained in a small research plot mowed at 2.54 centimeters (cm) for eight years. Then, in 1983, 'MoBuff' was established for fourteen years. Maintenance in the study has included close mowing at 1.28 to 1.90 cm, fertilization with only 98 kilograms nitrogen per hectare per year (kg N per ha/yr), and irrigation to the extent needed to prevent dormancy of the bermudagrasses in the study.

Subsequently, the 'MoBuff' genotype was propagated vegetatively by stolons (or runners) and pre-rooted plugs to provide stock for other comparisons.

Prior to this work, a number of other buffalograsses had been developed for use in the plains states. However, 'MoBuff' is the only warm-season grass genotype known to have a twenty-two-year record of cold hardiness in central Missouri.

The advantageous attributes of 'MoBuff' are early greenup and demonstrated long-term winter hardiness in Missouri compared with bermudagrass, zoysiagrass, and many other boffalograss genotypes.

'MoBuff' may be slower than some other buffalograsses to establish vegetatively. Buffalograsses, including 'MoBuff', may not always provide acceptable-quality turf. Quality is dependent upon prevailing environmental conditions. In particular, an overabundance of moisture during the growing season can be especially detrimental in the Midwest Transition Araa, and the quality of many buffalograsses, including 'MoBuff', may be only fair to poor during wet summers in the Midwest Transition Area, as was demonstrated in 1995 testing in New Franklin, Mo.

The qualities of 'MoBuff' buffalograss have been investigated at three different research sites — in New Franklin, Mo., Mt. Vernon, Mo. and Columbia, Mo. Data in Table 1 compares qualities of 'MoBuff' buffalograss with those of commonly used buffalograss cultivars 'Prairie' and 'Texoka' (data selected from the Missouri National Turf Evaluation Program — "NTEP"— study) at the New Franklin, Mo. Horticulture Research Center in 1994.

TABLE 1

QUALITIES† OF 'MOBUFF'* BUFFALOGRASS COMPARED WITH THE COMMONLY USED CULTIVARS 'PRAIRIE'* AND 'TEXOKA'* (Data selected from the Missouri NTEP Study at New Franklin, Missouri Horticulture Research Center.

| Genotype Entry | Genetic Color 7/94 | Greenup 4/94 | Leaf Texture 7/94 | Quality 5/94 |
|---|---|---|---|---|
| 'MoBuff' | 7.5 | 4.0 | 7.0 | 5.3 |
| 'Prairie' | 6.0 | 2.0 | 7.6 | 4.3 |
| 'Texoka' | 7.0 | 3.6 | 7.3 | 5.6 |
| $LSD_{0.05}$** | 0.15 | 0.19 | 0.14 | 0.31 |
| **Genotype Entry** | **Quality 6/94** | **Quality 7/94** | **Density 5/94** | **Density 7/94** |
| 'MoBuff' | 5.5 | 5.8 | 5.3 | 5.8 |
| 'Prairie' | 6.3 | 5.7 | 4.3 | 6.0 |
| 'Texoka' | 6.0 | 6.0 | 5.0 | 6.0 |
| $LSD_{0.05}$** | 0.30 | 0.29 | 0.25 | 0.31 |

†The rating scales of genetic color, greenup, leaf texture, quality and density are from 1 to 9; with 9 being the best and 1 being the worst.
*'Prairie' and 'Texoka' were established in Summer 1991; 'MoBuff' was established in Summer 1993. Data were taken by Dr. Ken Hunt, Horticulture Department, University of Missouri-Columbia.
**The statistic reported here is the least significant difference (LSD) between means that would be statistically significant in inferential statistics, using an "F" test, at the 0.05 level - that is, if the means differ by at least the $LSD_{0.05}$, then one can infer that the difference is statistically significant.

The rating sclaes of genetic color, greenup, leaf texture quality and density are from 1 to 9; with 9 being the best and 1 being the worst. The stands of 'Prairie' and 'Texoka' were established in summer 1991. 'MoBuff' was established in summer 1993. The data show 'MoBuff' having better genetic color, spring greenup and spring density (i.e., density measured in May) than either 'Prairie' or 'Texoka'.'Prairie' and 'Texoka' had comparable (slightly better in some cases, slightly worse in others) leaf texture, quality and summer density (i.e., density measured in July) when compared to 'MoBuff'.

TABLE 2

GREENUP, QUALITY, DENSITY AND PERCENT TURF COVER OF 'MOBUFF'* BUFFALOGRASS COMPARED WITH THE COMMONLY USED CULTIVARS 'PRAIRIE'* AND 'TEXOKA'* (DATA SELECTED FROM THE MISSOURI NTEP STUDY) AT SOUTHWEST RESEARCH CENTER, MT. VERNON, MISSOURI.

| GENOTYPE ENTRY | GREENUP | QUALITY | DENSITY | % COVER |
|---|---|---|---|---|
| 'MoBuff' | 8.0 | 7 | 5 | 60 |
| 'Prairie' | 5.0 | 4 | 4 | 36 |
| 'Texoka' | 6.0 | 4 | 4 | 36 |
| $LSD_{0.05}$ | 3.0 | 1.3 | 3 | 15.0 |

*'Prairie' and 'Texoka' were established during Summer of 1991; 'MoBuff' was established during Summer of 1993.
Data were taken by Mr. Dan Wooley, Southwest Research Center, Mt. Vernon, Missouri.

Data in Table 2 show a comparison of the greenup, quality, density and percent turf cover of 'MoBuff' buffalograss compared with the commonly used cultivars 'Prairie' and 'Texoka' (data selected from the Missouri NTEP study) at Southwest Research Center, Mt. Vernon, Mo. The plots of 'Prairie' and 'Texoka' were established during summer of 1991. 'MoBuff' was established during summer of 1993.

TABLE 3

QUALITY OF 'MOBUFF'* BUFFALOGRASS COMPARED WITH THE COMMONLY USED CULTIVARS 'PRAIRIE'* AND 'TEXOKA'* (DATA SELECTED FROM THE MISSOURI NTEP STUDY) AT THE HORTICULTURE AND AGROFORESTRY RESEARCH CENTER, NEW FRANKLIN, MISSOURI.

| GENOTYPE ENTRY | QUALITY 6/94 |
|---|---|
| 'MoBuff' | 5 |
| 'Prairie' | 4 |
| 'Texoka' | 4 |
| $LSD_{0.05}$ | 0.30 |

*'Prairie' and 'Texoka' were established during Summer of 1991; 'MoBuff' was established during Summer of 1993.
Data were taken by Dr. John Dunn, Horticulture Department, University of Missouri-Columbia.

Data in Table 3 show a comparison of the quality of 'MoBuff'* buffalograss compared with the commonly used cultivars 'Prairie'* and 'Texoka'* (data selected from the Missouri NTEP study) at the Horticulture and Agroforestry Research Center, New Franklin, Mo.

TABLE 4

1995 QUALITY OF 'MOBUFF' AND OTHER SELECTED COMMERCIALLY AVAILABLE BUFFALOGRASS GENOTYPES AT NEW FRANKLIN, MISSOURI RESEARCH CENTER.

| GENOTYPE | QUALITY † | | | |
|---|---|---|---|---|
| ENTRY | JUNE | JULY | AUGUST | SEPTEMBER |
| 'MoBuff' | 6.0 | 4.3 | 2.7 | 2.3 |
| '609' | 4.0 | 3.3 | 2.3 | 2.0 |
| 'Prairie' | 5.3 | 4.7 | 4.3 | 4.7 |
| 'SHARP'S IMPROVED' | 5.3 | 5.0 | 4.3 | 4.7 |
| 'TOP GUN' | 5.0 | 3.7 | 2.7 | 3.3 |
| 'Texoka' | 5.3 | 5.0 | 4.0 | 5.0 |

†Rating scale for Quality, 1 to 9 (9 = Best)
*'MoBuff' was established one year after the other entries.

Data in Table 4 show measurements of the 1995 quality of 'MoBuff' and other selected commercially available buffalograss genotypes at New Franklin, Mo. Research Center. 'MoBuff' showed better spring quality than the other varieties tested. However, the weather during this period at this site was quite wet for buffalograss, and the quality of all buffalograss varieties suffered to some extent as a result.

The soil type at the Mt. Vernon, Mo. test site is typically Creldon silt loam, fine mixed, mesic Mollic Fragredalfs. The soil type at the New Franklin, Mo. test site is typically Menfro fine silty, mixed mesic typic Hapludalfs.

TABLE 5

FALL COLOR AND QUALITY OF 'MOBUFF' BUFFALOGRASS TESTED WITH BERMUDAGRASS AT THE UMC TURFGRASS RESEARCH CENTER, COLUMBIA, MISSOURI 1990, 1993.

| GENOTYPE ENTRY | FALL COLOR† 10/90 | QUALITY* 7/90 | QUALITY 6/93 |
|---|---|---|---|
| 'MoBuff' | 6 | 5 | 6 |
| 'MIDLAWN' | 5 | 2 | 5 |
| 'KSU A-29' | 5 | 4 | 5 |
| 'MIDIRON' | 4 | 5 | 5 |
| 'MIDFIELD' | 4 | 3 | 5 |
| 'KSU S-16' | 5 | 3 | 5 |

TABLE 5-continued

FALL COLOR AND QUALITY OF 'MOBUFF' BUFFALOGRASS TESTED WITH BERMUDAGRASS AT THE UMC TURFGRASS RESEARCH CENTER, COLUMBIA, MISSOURI 1990, 1993.

| | | | |
|---|---|---|---|
| 'MICH C-53' | 5 | 4 | 3 |
| 'VAMONT' | 1 | 2 | 1 |
| 'MSDA C-TRANS' × 'BERLIN 12-16' | 5 | 3 | 4 |
| 'GUYMAN' | 5 | 3 | 4 |
| 'HICKORY HILLS' | 4 | 2 | 5 |
| $LSD_{0.05}$ | 1.2 | 1.1 | 1.3 |

| GENOTYPE ENTRY | QUALITY 7/93 | QUALITY 8/93 | QUALITY 9/93 |
|---|---|---|---|
| 'MoBuff' | 6 | 6 | 6 |
| 'MIDLAWN' | 5 | 5 | 5 |
| 'KSU A-29' | 5 | 5 | 5 |
| 'MIDIRON' | 5 | 5 | 5 |
| 'MIDFIELD' | 4 | 5 | 5 |
| 'KSU S-16' | 4 | 5 | 5 |
| 'MICH C-53' | 3 | 3 | 3 |
| 'VAMONT' | 1 | 1 | 1 |
| 'MSDA C-TRANS' × 'BERLIN 12-16' | 4 | 5 | 5 |
| 'GUYMAN' | 3 | 4 | 4 |
| 'HICKORY HILLS' | 5 | 6 | 5 |
| $LSD_{0.05}$ | 1.5 | 1.2 | 1.2 |

†Rating scale for Color and Quality, 1 to 9 (9 = Best)
*Follows period of drought stress.
Data was taken by Dr. John Dunn, Horticulture Department, University of Missouri-Columbia.

TABLE 6

SPRING GREENUP, 1986–1994, OF 'MOBUFF' AND BERMUDAGRASS ENTRIES, COLUMBIA, MISSOURI.

| | GREENUP (in %) | | | | |
|---|---|---|---|---|---|
| GENOTYPE ENTRY | 6/5/86 | 5/1/87 | 5/2/88 | 5/9/89 | 5/8/90 |
| 'MoBuff' | 67 | 68 | 99 | 98 | 97 |
| 'MIDLAWN' | 58 | 53 | 27 | 40 | 18 |
| 'KSU A-29' | 65 | 62 | 8 | 22 | 2 |
| 'MIDIRON' | 30 | 62 | 35 | 60 | 47 |
| 'MIDFIELD' | 67 | 57 | 10 | 38 | 12 |
| 'KSU S-16' | 10 | 68 | 18 | 38 | 6 |
| 'MICH. C-53' | 83 | 68 | 38 | 53 | 49 |
| 'VAMONT' | 8 | 27 | 18 | 13 | 4 |
| 'USDA C-TRANS' × 'BERLIN 12-16' | 50 | 55 | 45 | 32 | 22 |
| 'GUYMON' | — | — | 25 | 55 | 40 |
| 'HICKORY HILLS' | — | — | — | — | 25 |

| | GREENUP (in %) | | | |
|---|---|---|---|---|
| GENTOTYPE ENTRY | 4/30/91 | 5/5/92 | 5/6/93 | 5/28/94 |
| 'MoBuff' | 88 | 92 | 99 | 90 |
| 'MIDLAWN' | 7 | 35 | 70 | 27 |
| 'KSU A-29' | 9 | 27 | 48 | 57 |
| 'MIDIRON' | 18 | 50 | 63 | 37 |
| 'MIDFIELD' | 15 | 38 | 48 | 53 |
| 'KSU S-16' | 5 | 28 | 55 | 17 |
| 'MICH. C-53' | 20 | 22 | 53 | 17 |
| 'VAMONT' | 0 | 2 | 20 | 0 |
| 'USDA C-TRANS' × 'BERLIN 12-16' | 25 | 47 | 63 | 8 |
| 'GUYMON' | 8 | 28 | 25 | 8 |
| 'HICKORY HILLS' | 7 | 63 | 37 | 13 |

Data were taken by Dr. John Dunn, Horticulture Department, University Missouri-Columbia.

Data in Table 5 compares fall color and quality of 'MoBuff' buffalograss tested with Bermudagrass at the University of Missouri-Columbia (UMC) Turfgrass Research Center, Columbia, Mo. 1990, 1993 in field tests. These tests have shown 'MoBuff' to have better color and quality relative to the hot-weather Bermudagrasses.

Data in Table 6 compares spring greenup of 'MoBuff' buffalograss from 1986 to 1994 tested with Bermudagrass at the University of Missouri-Columbia (UMC) Turfgrass Research Center, Columbia, Mo. 1990, 1993 in field tests. These tests have shown MoBuff to have better color and quality relative to the hot-weather Bermudagrasses.

TABLE 7

LEAF TILLER WIDTH CHARACTERISTICS OF BUFFALOGRASS

| GENOTYPE/ | WINTER 1995 LEAF TILLER WIDTH | | | |
|---|---|---|---|---|
| | RIGHT TILLER | | LEFT TILLER | |
| CULTIVAR | TILLER 1 | TILLER 2 | TILLER 1 | TILLER 2 |
| 'MoBuff' | 1.5 | 1.4 | 1.5 | 1.4 |
| 'Texoka' | 1.5 | 1.6 | 1.6 | 1.7 |
| '$MO_1$' | 1.2 | 1.2 | 1.3 | 1.2 |
| '$MO_2$' | 1.3 | 1.2 | 1.2 | 1.3 |
| $LSD_{0.05}$ | 0.3 | 0.3 | 0.4 | 0.3 |

*Average of 20 measurements (Measurements in millimeters)

TABLE 8

LEAF TILLER LENGTH CHARACTERISTICS OF BUFFALOGRASS

| GENOTYPE/ | WINTER 1995 LEAF TILLER LENGTH* | | | |
|---|---|---|---|---|
| | RIGHT TILLER | | LEFT TILLER | |
| CULTIVAR | TILLER 1 | TILLER 2 | TILLER 1 | TILLER 2 |
| 'MoBuff' | 16 | 17 | 14 | 15 |
| 'Texoka' | 22 | 29 | 21 | 31 |
| '$MO_1$' | 14 | 17 | 16 | 16 |
| '$MO_2$' | 14 | 14 | 14 | 15 |
| $LSD_{0.05}$ | 4 | 4 | 5 | 5 |

*Average of 20 measurements (Measurements in millimeters)

Data in Tables 7 and 8 (respectively) show leaf tiller width and length (respectively) characteristics, in millimeters, of four buffalograss genotypes: 'MoBuff', 'Texoka', '$MO_1$', and '$MO_2$' ('$MO_1$' and '$MO_2$' are buffalograss varieties selected at University of Missouri).

TABLE 9

INTERNODE WIDTH* OF BUFFALOGRASS

| GENOTYPE/ CULTIVAR | WINTER 1995 INTERNODE 1 | INTERNODE 2 | INTERNODE 3 |
|---|---|---|---|
| 'MoBuff' | 0.9 | 0.9 | 0.8 |
| 'Texoka' | 0.8 | 0.9 | 0.9 |
| '$MO_1$' | 0.8 | 0.8 | 0.9 |
| '$MO_2$' | 0.7 | 0.7 | 0.8 |
| $LSD_{0.05}$ | 0.2 | 0.2 | 0.2 |

*Average of 20 measurements (measurements in millimeters)

TABLE 10

INTERNODE LENGTH* OF BUFFALOGRASS

| GENOTYPE/ CULTIVAR | WINTER 1995 INTERNODE 1 | INTERNODE 2 | INTERNODE 3 |
|---|---|---|---|
| 'MoBuff' | 27 | 29 | 27 |
| 'Texoka' | 53 | 53 | 64 |
| '$MO_1$' | 36 | 32 | 29 |
| '$MO_2$' | 37 | 34 | 36 |
| $LSD_{0.05}$ | 18 | 10 | 27 |

*Average of 20 measurements (measurements in millimeters)

Data in Tables 9 and 10 (respectively) show internode width and length (respectively) characteristics of four buffalograss genotypes: 'MoBuff', 'Texoka', '$MO_1$', and '$MO_2$'.

TABLE 11

Spikelet Length Characteristics of Buffalograss University of Missouri Greenhouse

| GENOTYPE/CULTIVAR | cm |
|---|---|
| 'MoBuff' | 2.5 |
| 'Texoka' | 10.6 |
| '$MO_1$' | 4.0 |
| '$MO_2$' | 5.0 |
| $LSD_{0.05}$ | 4.0 |

*Average of 20 measurements

TABLE 12

Inflorescence Height Characteristics of Buffalograss University of Missouri Greenhouse

| GENOTYPE/CULTIVAR | cm |
|---|---|
| 'MoBuff' | 2.0 |
| 'Texoka' | 8.0 |
| '$MO_1$' | 1.0 |
| '$MO_2$' | 3.0 |
| $LSD_{0.05}$ | 2.0 |

*Average of 20 measurements

Data in Table 11 and 12 (respectively) show spikelet length and inflorescence height (respectively) characteristics of four buffalograss genotypes: 'MoBuff', 'Texoka', '$MO_1$', and '$MO_2$'. As shown in Table 11, the spikelet length of 'MoBuff' is shorter than the other genotypes measured. As shown in Table 12, the average height of the 'MoBuff' inflorescence is 2 cm, providing a good aesthetic appearance as compared to other buffalograsses having a taller infloresence, for example, 'Texoka' which has an 8 cm average height.

TABLE 13

Comparison of ploidy level and chromosome number for 'MoBuff,' 'Hilite,' 'Prairie,' and 'Texoka' buffalograsses

| GENOTYPE/ CULTIVAR | Ploidy level | Chromosome number |
|---|---|---|
| 'MoBuff' | diploid | 20 |
| 'Hilite 25' | diploid | 20 |
| 'Hilite 15' | diploid | 20 |
| 'Prairie' | tetraploid | 40 |
| 'Texoka' | hexaploid | 60 |

Data in Table 13 show ploidy of several genotypes, including 'MoBuff', 'Hilite 15' and 'Hilite 25' (see U.S. Plant Pat. Nos. 8,897 and 8,896, Sep. 13, 1994), 'Prairie', and 'Texoka' buffalograss varieties.

TABLE 14

| PERCENTAGE OF GROUNDCOVER LIVING | |
|---|---|
| GENOTYPE/ CULTIVAR | ESTABLISHED JUNE 1996, MEASURED SEPTEMBER 1996 |
| 'MoBuff' | 52% |
| 'NE-609' | 48% |
| 'MIDGET' | 46% |
| 'NE-378' | 43% |
| $LSD_{0.05}$ | 17% |

Data in Table 14 show the survival rates, in terms of percentages of groundcover living, for four genotypes of buffalograsses. Each stand was established in June 1996, and each was then measured in September 1996. While the 'MoBuff' variety showed the best percentage, its percentage was not significantly higher than the other varieties as measured (i.e., the 9% difference between 'MoBuff' at 52% and 'NE-378' at 43% was less than the Least Significant Difference (LSD) of 17% which would be needed to indicate an inferred statistically significant difference in this measurement).

TABLE 15

Comparison of summer and winter leaf colors for 'MoBuff' and 'Texoka' buffalograsses

| GENOTYPE/ CULTIVAR | Winter Leaf Color | Summer Leaf Color | Summer Interlode Stolon Color |
|---|---|---|---|
| 'MoBuff' | Apricot color 609/3 page 70* | Spinach green 960/1 page 187* | Uranium green 63/2 page 63* |
| 'Texoka' | Naples yellow 403 page 121* | Fern green 862/1 page 186* | Erythrite Red 0027/1 page 190* |

*Page numbers from R.H.S. Colour Chart mentioned in the text.

Data in Table 15 show summer and winter colors of 'MoBuff' as compared to 'Texoka'. The color designations noted above were assigned according to the R.H.S. Colour Chart, published in 1938 by The Royal Horticultural Society, London, England. The node pigmentation of 'MoBuff' is typically fern green 0862, page 186, Chart II, R.H.S. Colour Chart.

Figure 1:
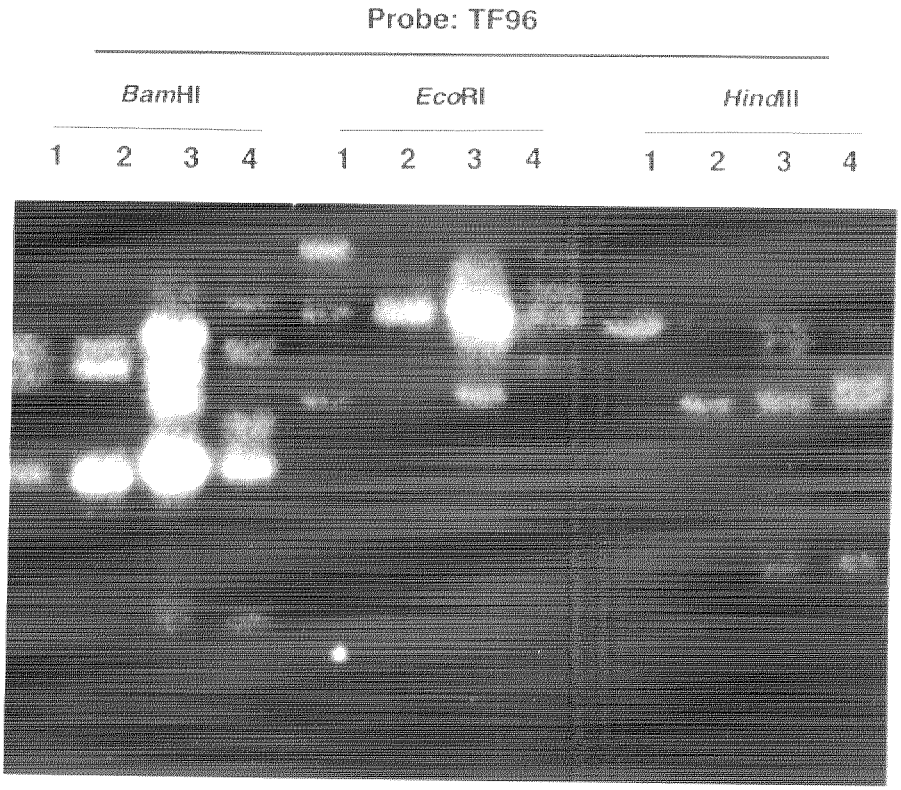
FIG. 1 depicts the autoradiograph of buffalograss DNAs probed with a tall-fescue clone 'TF96'.

FIG. 1 depicts the autoradiograph of buffalograss genetics probed with a tall-fescue clone 'TF96', showing three markers: BamHI, EcoRI, and HindIII. Each of the three columns labeled "1" are '$MO_1$', columns labeled "2" are '$MO_2$', columns labeled "3" are 'Texoka', and columns labeled "4" are 'MoBuff'.

FIG. 2 is a photograph that depicts a rectangle of sod of the buffalograss variety 'MoBuff' taken into a greenhouse in mid-winter alongside a similar piece of the variety 'Texoka' for comparison of greenup. Each of the rectangles was dug up at the same time in December 1996, and moved to the same indoors greenhouse setting to compare greenup.

FIG. 3 is a photograph that depicts a rectangle of 'MoBuff' after greenup in a greenhouse.

Figure 4:
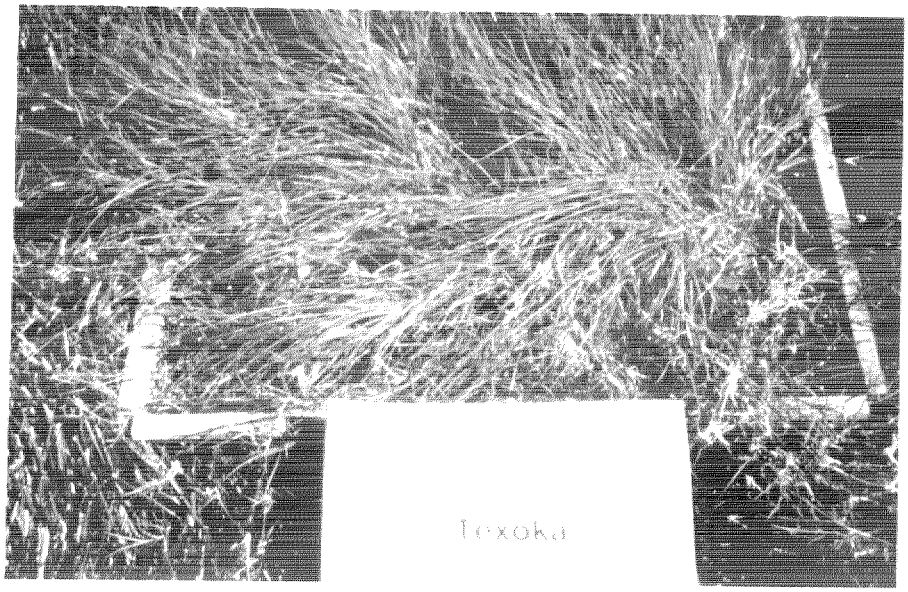
FIG. 4 is a photograph that depicts a rectangle of 'Texoka' after greenup in a greenhouse under the same conditions as the 'MoBuff' of FIG. 3.

FIG. 4 is a photograph that depicts a rectangle of 'Texoka' after greenup in a greenhouse under the same conditions as the 'MoBuff' of FIG. 3.

FIG. 5 is a photograph that depicts in detail the structure of a portion of a single plant of 'MoBuff' and a ruler marked in inches. 'MoBuff' tends to propagate more than one stolon (or runner) from each node, in contrast to other buffalograsses grown in the same circumstances that propagate a single stolon from each node (for example, see FIG. 6). When 'MoBuff' sends more than one stolon from a node, usually two stolons emerge with one noticeably longer than the other. For example, see FIG. 5 where the 'MoBuff' plant is growing from left-to-right, and the node above the ruler at 9⅛ inches (23.2 cm) has sent one stolon/runner shown in the photograph slightly down and to the left to about 7⅝ inches (19.4 cm), and has sent a second stolon/runner shown in the photograph slightly up and to the left to about 7¼ inches (18.5 cm).

Further, the leaflets that sheath the nodes of a 'MoBuff' plant tend to retain the green color of the other leaves of the plant, providing a greener overall appearance to a 'MoBuff' lawn. 'MoBuff' node leaflets (non-dormant summer color) are typically fern green 0862, page 186, Chart II, R.H.S. Colour Chart. In contrast, the leaflets that sheath the nodes of a 'Texoka' plant grown in similar circumstances tend to be a light tan color (See FIG. 6), detracting from an overall green appearance of a lawn.

Figure 6:
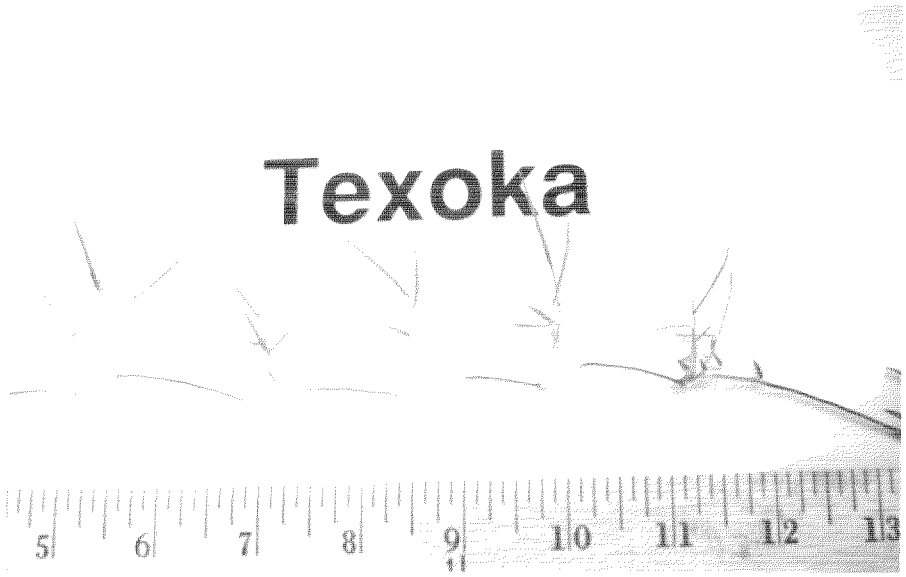
FIG. 6 is a photograph that depicts in detail the structure of portion of a single plant of 'Texoka' grown under the same conditions as the 'MoBuff' of FIG. 5.

FIG. 6 is a photograph that depicts in detail the structure of a portion of a single plant of 'Texoka' grown under the same conditions as the 'MoBuff' plant of FIG. 5.

Classification:

*Botanic.*—*Buchloe dactyloides* (Nutt) Engelm.

*Chromosome number.*—2n chromosomes=20 (diploid).

*Form.*—Monocot gramineae.

*Growth habit.*—The variety grows as a perennial female plant, with a stoloniferous growth habit that allows it to be propagated vegetatively. The variety is able to spend under non-competitive conditions when conditions are favorable for stolon production.

Adaptation: Canadian border to central Mexico, with optimum growth seen in the central great plains. The variety is very well adapted to the arid Great Plains United States, including those areas having cold winters such as central Missouri.

'MoBuff' will produce a dense, short, fine-textured turf with good color, including leaflets on the stolon nodes, throughout most of the growth season. The stolons (or runners) grow laterally above the ground, but grow low and close to the ground, thus providing a better aesthetic appearance compared to varieties such as 'Prairie' whose stolons grow higher from the ground and are thus more visible. Further, the low habit of 'MoBuff' stolons provides the advantage that the stolons are less likely to be clipped when the lawn is mowed, in contrast to the higher habit of the stolons in the 'Prairie' variety.

'MoBuff' is better than 'Prairie' and 'Texoka' for primary and secondary stolon number. The primary stolon length of 'MoBuff' is comparable to that of 'Texoka'. The internode width of 'MoBuff' depends in the density of the lawn, and will be thinner in a more dense lawn.

The new 'MoBuff' variety and two other Buffalograsses were compared in a turf evaluation of overall month-to-month growth quality, leaf texture, density, and seasonal color at the New Franklin, Mo. test site (See Table 1, above). The new 'MoBuff' variety and two other buffalograsses were compared in a turf evaluaton of overall greenup, growth quality, density, and percentage cover at the Mt. Vernon, Mo. test site (See Table 2, above).

Blade:

*Shape.*—Long and slender.

*Length.*—About 13 cm to 15.3 cm, typical 14 cm.

*Width.*—About 1.4 mm to 1.7 mm, typical 1.6 mm.

*Hairs.*—Both abaxial and adaxial hairs.

Mature plant height: About 12.5 cm to about 20 cm with fertilization, about 15 cm typical.

Primary internode: Length for the third internode from the tip ranges from about 2.5 cm to about 3.5 cm, about 2.7 cm typical. For the fourth internode from the tip, a typical internode length is 3.5 cm, with a range from about 2.7 cm to 5.1 cm. The primary internode diameter for the third internode from the tip is 1.0 mm. For the fourth internode from the tip, the primary internode diameter is typically 0.9 mm, with a range from about 0.7 mm to 1.1 mm.

Node pigmentation: Predominantly fern green 0862, page 186 of Chart II, R.H.S. Colour Chart.

Stolon color: Non-dormant is typically green, having the color designation uranium green 63/2 page 63, Chart I, R.H.S. Colour Chart.

Leaf color: The summer (non-dormant) leaf color is spinach green (960/1 on page 187). The winter (dormant) leaf color is apricot color (609/3 on page 70). The color designations noted above were assigned according to the R.H.S. Colour Chart, first published in 1938 by The Royal Horticultural Society, London, England.

Soils: Silty loams to fine silt soils with slightly acid to alkaline pH. 'MoBuff' does not grow well in sand.

Female inflorescence: Very few, less than about 10%, and thus not well suited for seed production. As shown in Table 12, the average height of the inflorescence is 2.0 cm. 0 to 2 per square foot, typically 1. The flower parts are typically 2 cm high (see Table 12), at the low end of the range for similar varieties.

'MoBuff' buffalograss is a vegetatively propagated female plant. The above-noted characteristics of this variety breed true to form in succeeding vegetatively propagated generations. The parentage of 'MoBuff' is unknown, although the plant from which 'MoBuff' was derived was obtained in 1974 from an established central Missouri lawn in the town of Columbia Mo. The established lawn contained both buffalograss and Kentucky bluegrass. The original plant was selected from the lawn at the junction of a driveway and a sidewalk because of its green color compared to the other grass variety or varieties in the lawn. Over the years, the lawn had been irrigated and mowed from time to time. The exact nature of the original buffalograss in the lawn is not known.

The new variety was isolated from the established central Missouri lawn as follows: The original plant was established in a small research plot and allowed to reach full ground cover. For eight years, the research plot was mowed at 2.54 cm. Starting in 1983, 'MoBuff' was mowed to a shorter height by close mowing at 1.28 to 1.90 cm, fertilization with only 98 kilograms nitrogen per hectare per year (kg N per ha/yr), and irrigation to the extent needed to prevent dormancy of bermudagrasses in a comparative study. Subsequently, the 'MoBuff' genotype was propagated vegetatively by stolons and pre-rooted plugs to provide stock for other comparisons.

What is claimed is:

1. A new and distinct variety of buffalograss substantially as shown and described.

* * * * *

Autoradiograph of Buffalograss DNAs probed with tall fescue clone TF96. 1=MO1; 2=MO2; 3=Texoka; 4=MoBuff.